United States Patent [19]

Cheetham

[11] 4,362,242
[45] Dec. 7, 1982

[54] MULTI-COMPARTMENT CONTAINER FOR STORING AND MIXING DENTAL AMALGAM INGREDIENTS, AND METHOD OF USING SUCH A CONTAINER

[76] Inventor: Jeffery J. Cheetham, 5 Brunsdon St., Bayswater, Victoria 3153, Australia

[21] Appl. No.: 133,262

[22] Filed: Mar. 24, 1980

[30] Foreign Application Priority Data

Apr. 10, 1979 [AU] Australia ............................ PD8360

[51] Int. Cl.³ .......................................... B65D 25/08
[52] U.S. Cl. ................................... 206/219; 366/602; 215/DIG. 8
[58] Field of Search ....................... 206/219, 220, 568; 366/602; 215/DIG. 8

[56] References Cited

U.S. PATENT DOCUMENTS 2,487,236 11/1949 Greenberg .......................... 206/220
4,182,447 1/1980 Kay ..................................... 206/220

Primary Examiner—Joseph Man-Fu Moy
Attorney, Agent, or Firm—William R. Hinds

[57] ABSTRACT

The present invention provides a self activating multicompartment container comprising an outer wall defining a chamber, a partition dividing the chamber into first and second compartments, a first, high specific gravity liquid component of a composition contained in the first compartment and a second component of the composition contained in the second compartment, wherein the container may be subjected to rapid oscillatory motion so as to cause the high specific gravity liquid component to rupture the partition so that admixture of the components takes place.

The container of the invention is useful for storage, transportation and admixture of the components of compositions in which one component is a high specific gravity liquid such as mercury, an example of such compositions being dental amalgams. The container may be activated by being inserted in a vibratory mixture and does not require the use of a plunger.

14 Claims, 1 Drawing Figure

U.S. Patent   Dec. 7, 1982   4,362,242
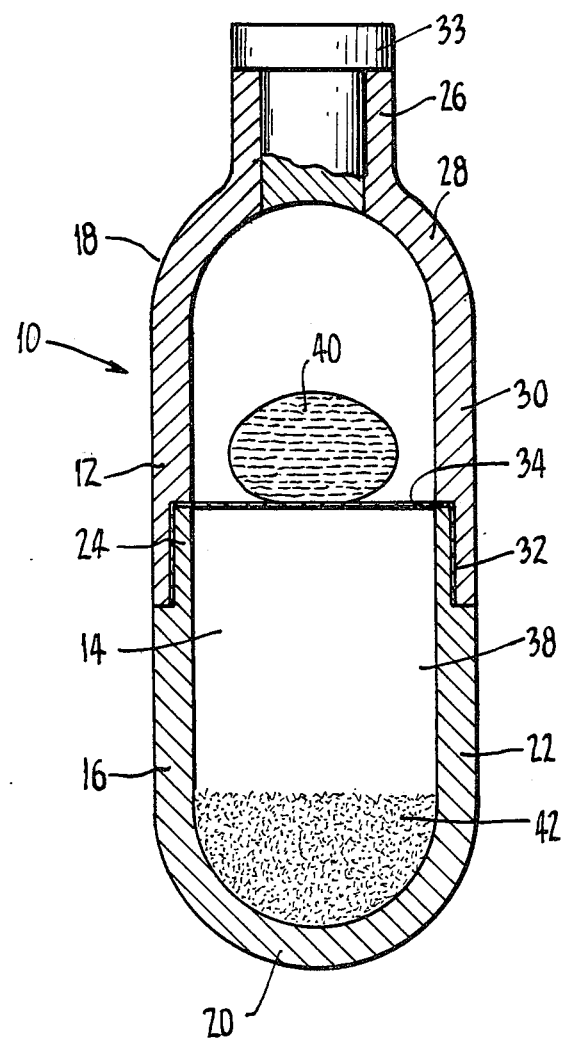

MULTI-COMPARTMENT CONTAINER FOR STORING AND MIXING DENTAL AMALGAM INGREDIENTS, AND METHOD OF USING SUCH A CONTAINER

The present invention relates to multi-compartment containers, particularly for dental purposes.

It is known to provide multi-compartment containers for transport and storage of components of compositions in separated condition, and for use in admixture of the components to form the composition. Typically, these containers comprise an outer wall defining a chamber which is separated into two compartments by means of a partition. An actuating means, such as a plunger, is provided for rupturing or dislodging the partition when it is desired to admix the components. The actuating means may rupture or dislodge the partition by hydrostatic pressure exerted through a liquid component contained in a compartment or it may rupture the partition by physically contacting the partition. When the partition has been ruptured, the container may be inserted in a vibratory mixer which subjects the container to a rapid sideways oscillation so as to ensure complete admixture of the components. The use of a plunger has a number of disadvantages depending on the design of the particular container such as incorporation of part of all of the partition in the mixture, passage of a liquid component between the plunger and the wall of the container or only a portion of a component passing through the ruptured partition for admixture.

The present invention provides self activating multi-compartment container for storage, transportation and admixture of the components of any form of composition in which one of the components is a high specific gravity liquid such as mercury. The container of the present invention is so constructed that it does not require a plunger to effect rupture of a partition to permit admixture of components contained in the container.

In accordance with the present invention there is provided a self activating multi-compartment container comprising an outer wall defining a chamber, a partition dividing the chamber into first and second compartments, a first, high specific gravity liquid component of a composition contained in the first compartment and a second component of the composition contained in the second compartment, wherein the container may be subjected to rapid oscillatory motion so as to cause the high specific gravity liquid component to rupture the partition so that admixture of the components takes place.

The container of the present invention is particularly useful for transport and storage and admixture of the components of dental amalgams which typically comprise an alloy component in the form of a powder and a liquid mercury component. As is well known when the mercury or alloy are admixed they rapidly interact to form an amalgam which sets within a short space of time to a hard mass. Thus, the components have to be transported and stored in separated condition. When the amalgam is required for use, the components are admixed and the mixture is used, such as for filling teeth, immediately.

In the container of the present invention, the first compartment contains a globule of a high specific density liquid such as mercury. When the container is placed in, for example, a vibratory mixer and subjected to a rapid oscillatory motion in a direction at an acute angle such as a right angle to the partition, the globule of liquid is caused to undergo a rapid oscillatory motion in sympathy with the motion of the container between the partition and the end wall of the compartment facing the partition. In a short space of time the globule acquires sufficient kinetic energy to break through the partition and to contact the other component. Vibratory mixing is continued for a time sufficient for complete admixture of the components as is known in the art and then the mixture is retrieved from the container for use.

The partition is typically formed from a plastics material and is extremely thin. Preferably, the partition is from 0.01-0.15 mm thick, more preferably from 0.012-0.025 mm thick. The choice of plastics material is not critical and polyethylene has been found to be suitable although other plastics materials can be used. It has been found that a low slip, low density polyethylene having a density of 0.92 and a melt index of 6.4 works particularly well in the container of the present invention.

It is preferred that the partition in the container be stretched tight. If the partition is not stretched tight, the motion of the globule can cause the partition to flex rather than rupture.

In a preferred embodiment of the present invention the container comprises two bowl shaped members which are joined together by any suitable means such as co-operating flanges. The partition is located between the members such as by being heat sealed to one of them or merely entrapped between them. One of the members may comprise a closure in the form of a plug to seal the container.

After admixture has taken place, the mixture is retrieved by separating the bowl shaped members and scooping out the mixture.

The present invention will now be described, by way of example, with reference to the accompanying drawing which is a schematic vertical section through a container in accordance with the present invention.

In the drawing, there is shown a container 10 comprising an outer wall 12 defining a chamber 14. The outer wall 12 comprises first and second bowl shaped members 16 and 18 respectively. The first bowl shaped member 16 comprises a curved bottom 20 and a cylindrical wall 22 integrally formed with and extending from the curved bottom 20. The cylindrical wall 22 terminates in a circular flange 24 extending around the inner side of the top of the cylindrical wall 22.

The bowl shaped member 18 comprises an upper cylindrical portion of small diameter 26, an intermediate curved portion 28 and a lower cylindrical wall 30 of the same diameter as the cylindrical wall 22. The cylindrical wall 30 terminates in a circular flange 32 extending around the outer side of the bottom of the cylindrical wall 30. The cylindrical portion 26 is sealed by a plug 33 which has an inner contour flush with the curved portion 28 to form a smooth interior.

The flanges 24 and 32 are arranged to be co-operatively engaged with the flange 32 fitting over the flange 24 so as to join the bowl members 16 and 18 together.

A partition 34 is tautly mounted on the flange member 24 and is secured in place by having its edges heat sealed to the flange member 24 or by merely having its edges trapped between the shoulders 24 and 32.

The partition divides the chamber 14 into a first compartment 36 and a second compartment 38. The first compartment 36 contains a globule of mercury 40 which may be of a size sufficient to form a quantity of amalgam sufficient for dental filling purposes. When the container 10 is, as shown, upright the globule 40 rests on the partition 34. Thus, the partition 34 needs to be continuous i.e. free from pin holes or other defects, substantially non-porous and of sufficient strength to support the globule 40.

The compartment 38 contains a quantity of alloy powder 42 sufficient to interact with the quantity of mercury in the globule 40 to form an amalgam.

The container 10 may be assembled by
 (1) placing the alloy powder 42 in the bowl member 16 which has the curved portion 20 lowermost;
 (2) stretching a plastic film over the flange 24 and heat sealing the edges of the film to the flange 24;
 (3) placing the bowl member 18 over the bowl member 16 with the flanges 24 and 32 in co-operative engagement;
 (4) inserting the globule 40 in the first compartment 36 through the cylindrical portion 26; and
 (5) sealing the first compartment with the plug 33.

It is to be understood that other methods and/or sequences of assembly can be employed depending on the specific construction of the container 10.

In use, the container 10 is placed between a pair of forks of a vibratory mixer with the plug 33 and curved bottom 20 in contact with the forks. The mixer is then activated so as to subject the container 10 to a rapid sideways oscillation. This causes the globule 40 to oscillate from end to end of the first compartment 36 impacting alternately against the curved bottom 28 and the inner end of the plug 33 and the partition 34. As the globule 40 picks up speed it acquires sufficient kinetic energy to burst through the partition 34 to contact the alloy powder 42. Vibratory mixing is continued until admixture of the components is complete. Then the container 10 is removed from the mixer and the bowl members 16 and 18 separated to enable the amalgam produced to be retrieved.

Modifications and variations such as would be apparent to a skilled addressee are deemed within the scope of the present invention. For example, the plug 33 could be omitted and the curved bottom 28 made complete in similar fashion to the curved bottom 20. In this case the container would be filled and assembled in the reverse sequence to that described above.

I claim:

1. A method of using a self activating multi-compartment container comprising a chamber, a thin, taut, rupturable partition dividing the chamber into first and second compartments, the first compartment containing a globule of liquid mercury and the second compartment containing a quantity of dental metallic alloy powder, both compartments being otherwise devoid of any actuating or rupturing means for rupturing or dislodging the partition, wherein the container is subjected to a rapid oscillatory motion in a direction substantially at right angles to the partition so as to cause the globule of mercury to acquire kinetic energy until the acquired kinetic energy is sufficient for the globule of mercury to rupture the partition and thus allow the mercury to contact the alloy powder, said rapid oscillatory motion being continued for a time sufficient to enable the mercury and alloy powder to become admixed to form a dental amalgam.

2. A method as claimed in claim 1, in which the partition is formed of a layer of plastics material.

3. A method as claimed in claim 2, in which the partition is from 0.01-0.15 mm thick.

4. A method as claimed in claim 2, in which the partition is from 0.012-0.025 mm thick.

5. A self activating multi-compartment container comprising an outer wall defining a chamber, a thin, taut, rupturable partition dividing the chamber into first and second compartments, the first compartment containing a globule of liquid mercury and the second compartment containing a quantity of dental metallic alloy powder, both compartments being of fixed volume and being otherwise devoid of any actuating or rupturing means for rupturing or dislodging the partition, the partition being tautly mounted such that when the container is subjected to a sufficient rapid oscillatory motion in a direction substantially at right angles to the partition the globule of mercury acquires sufficient kinetic energy to rupture the partition so that admixture of the components can take place.

6. A container as claimed in claim 5, in which the partition is formed of a layer of plastics material.

7. A container as claimed in claim 6, in which the partition is from 0.01-0.15 mm thick.

8. A container as claimed in claim 6, in which the partition is from 0.012-0.025 mm thick.

9. A container as claimed in claim 5, which comprises a pair of bowl shaped members each having a closed end and an open end wherein the bowl shaped members are joined together in abutting relation at their open ends.

10. A container as claimed in claim 9, in which the open ends of the bowl shaped members are formed with flanges, said flanges cooperatively engaging with one another to join the bowl shaped members together.

11. A container as claimed in claim 10, in which one of the bowl shaped members comprises a plug mounted in the closed end thereof.

12. A container as claimed in claim 10, in which the partition is secured in place by the abutting open ends of the bowl shaped members.

13. A method as claimed in claim 11 wherein the first compartment contains only a globule of liquid mercury, and the second compartment contains only dental metallic alloy powder.

14. A container as claimed in claim 5 wherein the first compartment contains only a globule of liquid mercury, and the second compartment contains only dental metallic alloy powder.

* * * * *